United States Patent [19]

Mehta

[11] Patent Number: 4,461,824
[45] Date of Patent: Jul. 24, 1984

[54] DIFFUSION CONTROL LAYERS IN DIFFUSION TRANSFER PHOTOGRAPHIC PRODUCTS

[75] Inventor: Avinash C. Mehta, Belmont, Mass.

[73] Assignee: Polaroid Corporation, Cambridge, Mass.

[21] Appl. No.: 454,447

[22] Filed: Dec. 29, 1982

[51] Int. Cl.³ .................. G03C 5/54; G03C 7/00; G03C 1/40; G03C 7/20
[52] U.S. Cl. .................. 430/215; 430/227; 430/505; 430/536
[58] Field of Search ........... 430/215, 536, 627, 629, 430/630, 227, 505

[56] References Cited

U.S. PATENT DOCUMENTS

| | | | |
|---|---|---|---|
| 4,288,523 | 9/1981 | Taylor | 430/215 |
| 4,297,431 | 10/1981 | Sullivan | 430/215 |
| 4,323,644 | 4/1982 | Nakamura et al. | 430/627 |
| 4,391,895 | 7/1983 | Schwarzel et al. | 430/215 |

Primary Examiner—Richard L. Schilling
Attorney, Agent, or Firm—Louis G. Xiarhos

[57] ABSTRACT

Polymers comprising recurring units having cyclic β-elimination moieties capable of undergoing β-elimination in an alkaline environment and are disclosed for use in diffusion control layers in diffusion transfer photographic products.

52 Claims, 4 Drawing Figures

DIFFUSION CONTROL LAYERS IN DIFFUSION TRANSFER PHOTOGRAPHIC PRODUCTS

BACKGROUND OF THE INVENTION

The present invention relates to photography and particularly to products adapted for employment in forming photographic diffusion transfer images. In particular, the present invention is directed toward the use of certain polymers in diffusion control layers of photographic diffusion transfer film units.

SUMMARY OF THE INVENTION

According to the present invention, there are disclosed certain polymers comprising recurring units having cyclic $\beta$-elimination moieties which undergo $\beta$-elimination in an alkaline environment. The polymers can be used to convert a layer comprising one or more of the polymers from a condition of impermeability to alkali or materials soluble in or solubilized by an aqueous alkaline processing composition to a condition of substantial permeability thereto. Polymeric layers having these $\beta$-eliminating polymers can be used as diffusion control interlayers or overcoats in photosensitive elements or negative components of diffusion transfer film units or as timing layers or overcoats in image-receiving elements or positive components of diffusion transfer film units.

Polymers useful according to the present invention for the provision of diffusion control layers in photographic products comprise certain essential recurring units having a cyclic $\beta$-elimination moiety capable of undergoing $\beta$-elimination in an alkaline environment. These polymers comprise recurring units of the formula

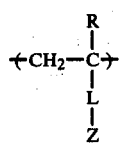

wherein

R is hydrogen, halogen (e.g., chloro) or lower alkyl (e.g., methyl);

L is an organic divalent linking group

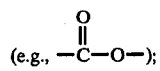

and

Z is a cyclic $\beta$-elimination moiety capable under alkaline conditions of undergoing a $\beta$-elimination reaction and having the formula

wherein
Y is

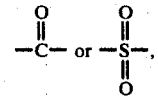

A represents the atoms necessary with Y to complete a four- to seven-membered ring structure, and D and E are independently hydrogen, methyl or phenyl, provided that not more than one of D and E is methyl or phenyl, or said cyclic $\beta$-elimination moiety is a moiety having the formula

wherein A and E together represent the atoms necessary to complete with the carbon atoms to which they are bonded a five-, six- or seven-membered ring structure, D represents hydrogen, methyl or phenyl and Y is an activating group for said $\beta$-elimination reaction.

For a fuller understanding of the nature and objects of the invention, reference should be had to the following detailed description taken in connection with the accompanying drawings.

THE DRAWINGS

DETAILED DESCRIPTION

Figure 1:
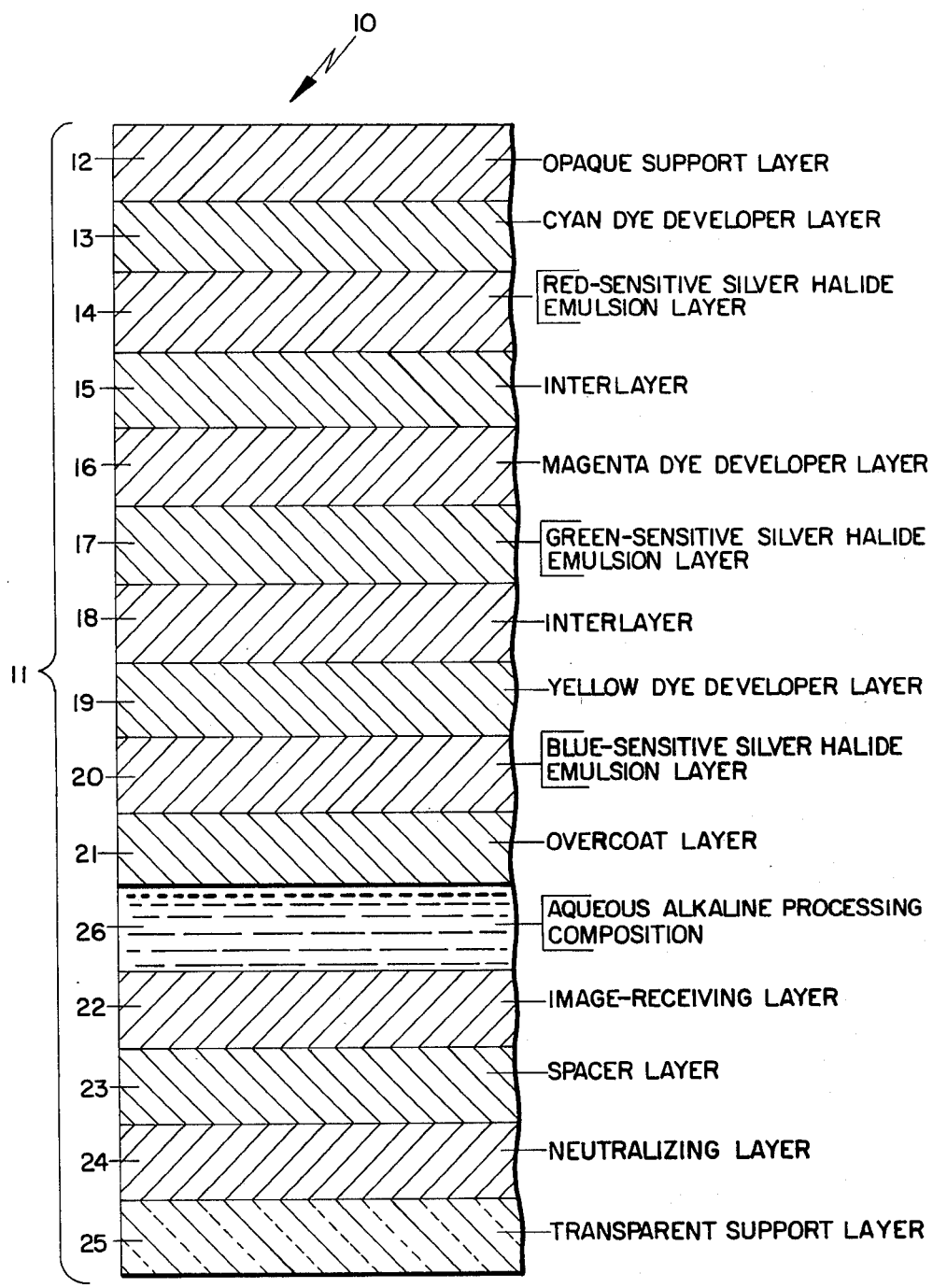
FIG. 1 is a cross-sectional view of a photographic film unit including diffusion control layers of this invention.

As mentioned hereinabove, the polymers herein described are capable of converting a layer comprising one or more of said polymers from a condition of impermeability to alkali or materials soluble in or solubilized by an aqueous alkaline processing composition to a condition of substantial permeability thereto by undergoing a $\beta$-elimination reaction in an alkaline environment. Polymeric layers comprising these polymers can be used as diffusion control layers in diffusion transfer film units. These diffusion control layers can be used as overcoats or interlayers in photosensitive elements and negative components of diffusion transfer film units or as timing layers or overcoats in image-receiving elements and positive components of diffusion transfer film units. The diffusion control layers hereof function by forming an impermeable "barrier" layer which prevents passage or diffusion therethrough of either alkali or materials soluble in or solubilized by an aqueous alkaline processing composition for a predetermined length of time during processing of the film unit and then converting over a relatively short time period to a condition of substantial permeability to these materials as a result of the polymers hereof undergoing $\beta$-elimination. These diffusion control layers are thus "hold-release" layers in that materials intended to be subject to diffusion control by the layer are "held" in place for a predetermined period of time and then are "released" in substantial quantity over a relatively short time period, i.e., allowed to rapidly diffuse through the layer. This desirable "hold-release" behavior may be contrasted with the diffusion control properties of those diffusion control layers which are not capable of undergoing a precipitous change in permeability but rather are initially permeable to some degree, and thus allow a slow leakage of material from the start of processing, and gradually become more permeable during the processing interval.

The polymers useful in the diffusion control layers hereof comprise essential recurring units capable of undergoing β-elimination and having the formula (I)

wherein R is hydrogen, halogen (e.g., chloro) or lower alkyl (e.g., methyl). In these recurring units, L is an organic divalent linking group, described in more detail hereinafter, and Z represents a cyclic β-elimination moiety which is capable of undergoing a β-elimination reaction under alkaline conditions and which, therefore, contains the atoms requisite for the conduct of such β-elimination reaction. The β-elimination Z moiety contains a cyclic structure and conforms to the formula (IIA or IIB):

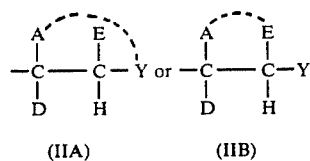

From inspection of the β-elimination moities of formulas (II A) and (II B), it will be seen that a proton is bonded in each instance to a carbon atom to which is also bonded an activating group, Y. This activating group activates abstraction of the labile proton atom under alkaline conditions, thus, effecting the conduct of a β-elimination mechanism.

In the β-elimination moiety of formula (II A), i.e., the moiety of the formula

Y represents either of the divalent radicals

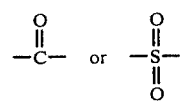

and is a part of a ring structure. A represents the atoms necessary with Y and the respective carbon atoms to which they are bonded to complete a four-to seven-membered ring structure. D and E independently represent hydrogen, methyl or phenyl, provided that not more than one of D and E is methyl or phenyl. Preferably, both D and E will be hydrogen. In the cyclic moiety of formula (II A), A can represent, for example, a divalent radical such as methylene, dimethylene, trimethylene or tetramethylene to complete, with the Y radical and the carbon atoms to which A and Y are bonded, a four-, five-, six- or seven-membered ring structure, respectively. Suitable β-elimination moieties of formula (II A) are the following moieties shown in formulas (III A) through (III D):

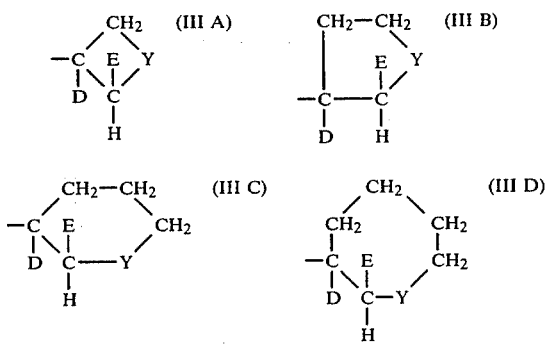

wherein, in each instance, Y is

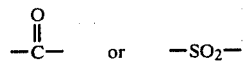

and A and D have the meanings aforedescribed. Preferably, in these β-elimination moieties, each of D and E will be hydrogen.

In general, a β-elimination reaction involves the elimination or removal of two groups from a parent molecule, these groups being substituted on adjacent atoms, i.e., beta to each other. The β-elimination reaction or removal results in the formation of a more unsaturated bond, usually a double bond, between the adjacent atoms. Referring to a polymer comprising the recurring units of formula (I) wherein the linking group L is

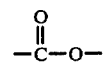

and the cyclic β-elimination moiety Z is a moiety of the formula (III B), the β-elimination reaction and mechanism can be represented as follows:

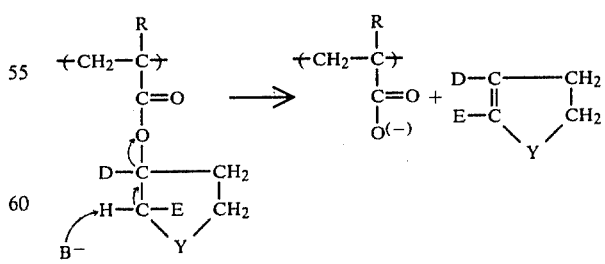

wherein B⁻ is an anionic base. The above reaction scheme shows the formation of an anionic polymer species as the result of the β-elimination. The anionic polymer unit is effectively a leaving group removed from the parent molecule (starting polymer) in order to effect formation of the double bond of the unsaturated cyclic compound, i.e., $$\begin{array}{c} D-C\!\!-\!\!-\!\!-CH_2 \\ \|\phantom{-C-}\phantom{-}| \\ E-C\phantom{-}\phantom{-}CH_2 \\ \diagdown\phantom{-}\diagup \\ Y \end{array}$$

Inspection of the β-elimination moiety of formula (II B), i.e., the moiety of the formula $$\begin{array}{cc} \overset{\frown}{A\phantom{-}E} \\ |\phantom{-}| \\ -C\!\!-\!\!-\!\!-C-Y \\ |\phantom{-}| \\ D\phantom{-}H \end{array} \qquad \text{(II B)}$$

will show that the β-elimination activating group can be present in the cyclic β-elimination moieties hereof as a ring substituent. In these β-elimination moieties, A and E together represent the atoms necessary to complete with the carbon atoms to which they are bonded a five-, six- or seven-membered ring structure. D represents hydrogen, methyl or phenyl and, preferably, is hydrogen. A and E together can represent, for example, trimethylene, tetramethylene or pentamethylene to provide a five-, six- or seven-membered ring structure, respectively. Suitable examples of β-elimination moities of formula (II B) are the following moieties shown in formulas (IV A) through (IV D):

(IV A)   (IV B)   (IV C)

(IV D)

wherein, in each instance, Y represents a β-elimination activating group.

In the β-elimination moieties of formula (II B), and those of formulas (IV A) through (IV D), Y represents any activating group which is photographically innocuous and which is capable of stabilizing the carbanionic species formed by abstraction of the acid-labile proton by an anionic base. A study of such activating groups has been provided by J. Crosby and C. J. M. Stirling in J. Chem. Soc., B, p. 671. Activating groups which can be used in the present invention include sulfones of the formula —$SO_2W$ wherein W is aryl, aralkyl, alkaryl, alkyl, amino, or substituted amino; carbonyl groups of the formula $$\begin{array}{c} O \\ \| \\ -C-T \end{array}$$

wherein T is hydrogen, alkyl, alkoxy, amino, or substituted amino; sulfoxide groups of the formula $$\begin{array}{c} O \\ \| \\ -S-G \end{array}$$

wherein G is aryl, alkyl, alkaryl or aralkyl; nitro; and cyano. Preferred groups which activate the β-elimination reaction are activating groups Y of the formula —$SO_2W$ wherein W is alkyl (e.g., methyl or ethyl) or alkaryl (e.g., p-tolyl).

In the polymers comprising the recurring units of formula (I), i.e., recurring units of the formula $$\begin{array}{c} R \\ | \\ \!\!+\!CH_2\!-\!\!\underset{|}{\overset{|}{C}}\!\!\!+ \\ L \\ | \\ Z \end{array}$$

L represents an organic divalent linking group. The nature of this linking group can vary and can, for example, be the group $$\begin{array}{c} O \\ \| \\ -C-O- \end{array}$$

characteristic of polymers derived from acrylic, methacrylic or 2-chloroacrylic acid. It will be appreciated that the nature of the linking group and its molecular configuration and size can influence the properties of the resulting polymer and the rate of the desired β-elimination and that choice of a suitable linking group may in part be influenced by synthetic considerations and ready availability of reactants for the production of the polymers hereof. The linking group $$\begin{array}{c} O \\ \| \\ -C-O- \end{array}$$

is a preferred linking group and can be introduced into the desired polymer from readily available acrylic materials.

The linking group can also be a group having the formula IV $$\begin{array}{ccc} O & R^2 & O \\ \| & | & \| \\ -C-N\!\!+\!\!C)_n\!\!-\!\!C-O- \\ & | & | \\ & R^1 & R^3 \end{array} \qquad \text{(V)}$$

wherein $R^1$ is hydrogen or lower alkyl; $R^2$ and $R^3$ can each independently be hydrogen; lower alkyl, e.g., methyl, ethyl, propyl, isopropyl; substituted lower alkyl, e.g., hydroxymethyl, hydroxyethyl, methylthioethyl; aryl, e.g., phenyl, naphthyl; alkaryl, e.g., tolyl; aralkyl, e.g., benzyl; cycloalkyl, e.g., cyclohexyl; or $R^2$ and $R^3$ together with the carbon atom to which they are bonded can constitute a carbocyclic or heterocyclic ring, e.g.

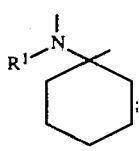

or $R^3$, when substituted on the methylene carbon atom next adjacent the nitrogen atom shown in formula (V) can be taken together with $R^1$ to form part of a substituted or unsubstituted N-containing ring, e.g.,

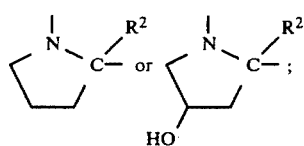

and n is a positive integer one to six. It will be appreciated that each of the n number of

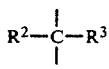

groups can be substituted the same or differently.

It will be appreciated that polymers having the recurring units of formula (I) wherein the linking group corresponds to that of formula (V) will comprise recurring units of the following formula (VI):

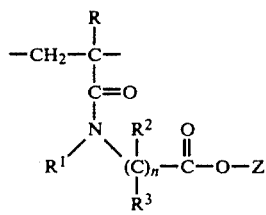

wherein R, $R^1$, $R^2$ and $R^3$ and Z have the meanings hereinbefore described.

Other suitable linking groups include those having the formula (VII):

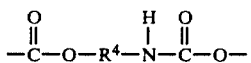

wherein $R^4$ is alkylene (e.g., ethylene). These linking groups which contain a carbamate moiety and can be derived from an isocyanatoalkyl ester, provide suitable linking to a β-elimination moiety. Polymers comprising the recurring units of formula (I) wherein this carbamate containing linking group is present will have the formula (VIII):

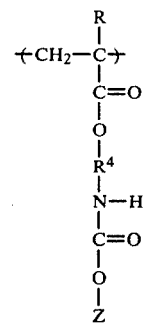

wherein R, $R^4$ and the cyclic β-elimination moiety Z have the meanings previously ascribed. Monomers and polymers having the above-described carbamate-containing linkage, i.e., polymers containing the recurring units of formula (VIII), and photographic products including such polymers are disclosed and claimed in the patent application of Lloyd D. Taylor, U.S. Ser. No. 454,448, filed of even date.

Other linking groups L can be suitably employed in the polymers hereof having the recurring units of formula (I) provided that the linking group does not adversely and unacceptably influence the desired β-elimination reaction required for the preparation of polymeric diffusion control layers as described herein and is photographically innocuous.

Examples of polymers that can be employed for the preparation of polymeric diffusion control layers in photographic products include polymers containing recurring units of the following formulas:

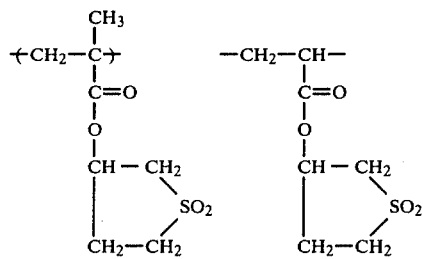

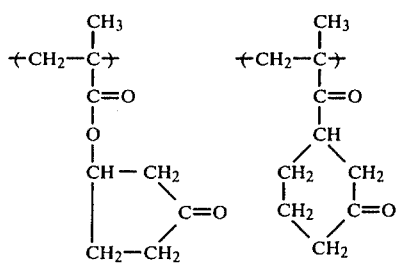

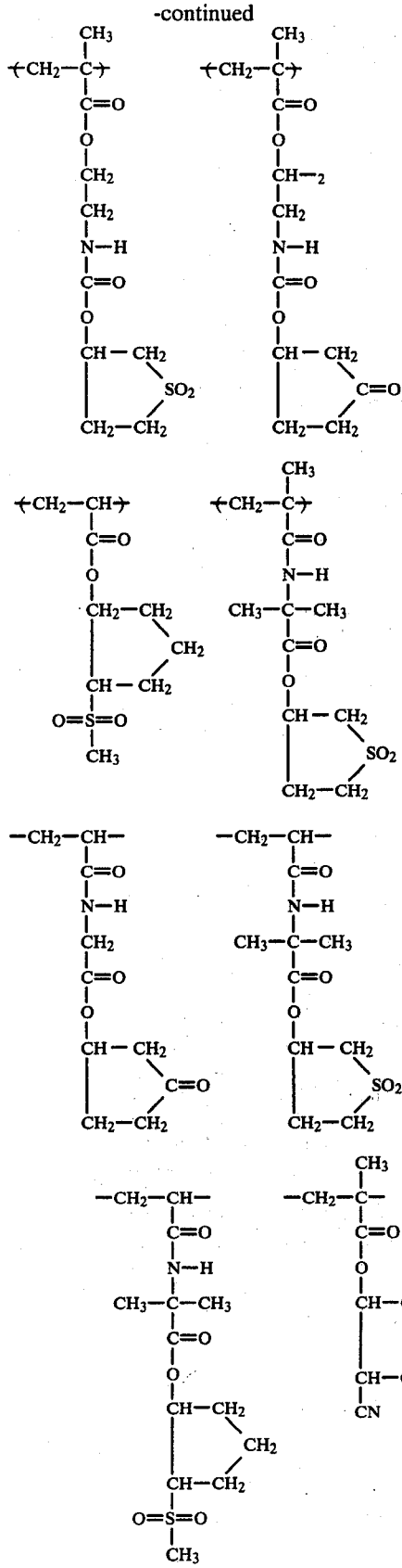

The polymers employed herein can be homopolymers or copolymers, including graft or block copolymers. The copolymers can contain units provided by copolymerization with various ethylenically unsaturated monomers such as alkyl acrylates, alkyl methacrylates, acrylamides, and methacrylamides. In general, these comonomeric units are utilized to provide particular predetermined properties to the polymer such as coatability and viscosity and, in particular, predetermined permeability characteristics.

In general, the polymers employed herein will contain the recurring β-elimination units in an amount sufficient to provide to a diffusion control layer the capacity for appreciable conversion from a relatively impermeable condition to a condition of relative permeability upon β-elimination and, thus, to provide functionality to the diffusion control layer as set forth herein. In the copolymers the proportion of the β-elimination units to the total units of the polymer will vary depending on the nature of the particular β-elimination units employed, the nature of comonomeric and polymeric materials utilized therewith, and upon the particular and predetermined permeability characteristics desired.

According to a preferred embodiment of the present invention, the polymers employed herein will comprise β-elimination units of formula (I) wherein R is hydrogen or methyl, the divalent linking group L is

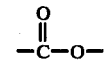

or a linking group having the formula (V) or (VII), and cyclic β-elimination moiety Z is a β-elimination moiety having the structure of formula (III B). These β-elimination units have the formula (IX).

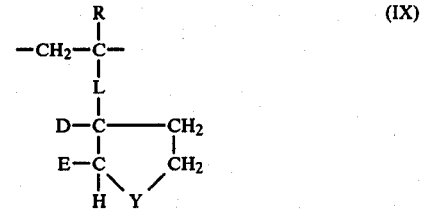

wherein, preferably, D and E are each hydrogen and Y is —SO₂.

As mentioned previously, the polymers of this invention can be copolymers comprising the β-elimination monomeric units and a variety of comonomeric units incorporated into the polymer to impart thereto predetermined properties. For example, the "hold time", i.e., the time interval during which a diffusion control layer remains impermeable during processing, can be affected by the relative hydrophilicity of the layer resulting from incorporation of a given comonomer or mixture of comonomers into the β-elimination polymer. In general, the more hydrophobic the polymer, the slower will be the rate of permeation of alkali into a diffusion control layer to initiate the β-elimination reaction, i.e., the longer the hold time. Alternatively, adjustment of the hydrophobic/hydrophilic balance of the polymer by inclusion of appropriate comonomeric units may be used to impart selective permeability characteristics to a diffusion control layer as appropriate for a given usage within a film unit. For example, as detailed hereinbelow, it is highly preferred that diffusion control interlayers in the negative component of the film unit be initially substantially permeable to alkali, water, and various other components of the processing composition while substantially impermeable to the image-providing materials of the film unit up to a predetermined point in the development process. Such selective permeability may be achieved in the present invention by inclusion of appropriate comonomeric units, generally of a relatively hydrophilic nature, into the β-elimination polymers hereof or, more particularly, by "balancing" the hydrophobic and hydrophilic moieties to achieve the desired permeability.

Examples of suitable comonomers for use in the present invention include acrylic acid; methacrylic acid; 2-acrylamido-2-methylpropane sulfonic acid; N-methyl acrylamide; methacrylamide; ethyl acrylate; butyl acrylate; methyl methacrylate; N-methyl methacrylamide; N-ethyl acrylamide; N-methylolacrylamide; N,N-dimethyl acrylamide; N,N-dimethyl methacrylamide; N-(n-propyl)acrylamide; N-isopropyl acrylamide; N-(β-hydroxy ethyl) acrylamide, N-(β-dimethylamino)acrylamide; N-(t-butyl) acrylamide; N-[β-(dimethylamino)ethyl]methacrylamide; 2-[2'-(acrylamido)ethoxy]ethanol; N-(3'-methoxy propyl)acrylamide; 2-acrylamido-3-methyl butyramide; acrylamido acetamide; methacrylamido acetamide; 2-[2'-methacrylamido-3'-methyl butyramido]acetamide; and diacetone acrylamide.

As examples of useful copolymers of this invention mention may be made of the polymers of:

(1) 3-sulfolanyl methacrylate/styrene (70/30 parts by weight):

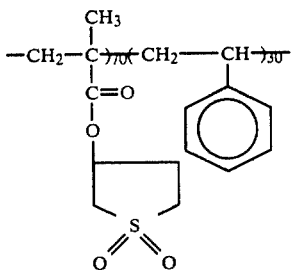

(2) 3-sulfolanyl methacrylate/diacetone acrylamide/styrene (56/30/14 parts by weight)
(3) 3-sulfolanyl-N-acrylyl-2-methylalanine/methyl methacrylate (56/44 parts by weight)
(4) N-(methacryloxyethyl)-3-sulfolanyl carbamate/styrene (70/30 parts by weight)

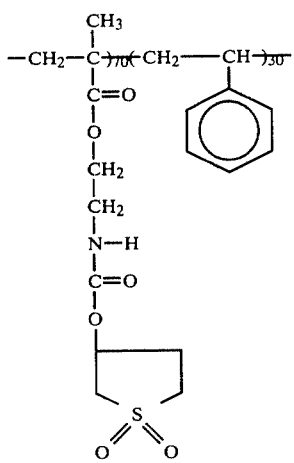

The β-elimination reaction which the β-elimination polymers of the diffusion control layers of this invention undergo ensures that those materials intended to be subject to diffusion control by the diffusion control layer are "held" in place for a predetermined period of time and then "released" over a relatively short time period, the polymer layer undergoing a relatively rapid increase in hydrophilicity and water swellability and, thus, permeability as a result of the β-elimination reaction. The predetermined hold time may be adjusted as appropriate for a given photographic process by means such as controlling the mole ratio or proportion of β-elimination units in the polymer; altering the thickness of the diffusion control layer; incorporating appropriate comonomeric units into the β-elimination to impart thereto a desired hydrophobic/hydrophilic balance or degree of coalescence; utilizing different activating groups Y to affect the rate of β-elimination; or utilizing other materials, particularly polymeric materials, in the diffusion control layer to modulate the permeation therethrough of alkali or aqueous alkaline processing composition, thereby altering the time necessary for substantial β-elimination to occur. This latter means of adjusting the hold time of the layer may include, for example, utilization of a matrix polymer material having a predetermined permeability to alkali or aqueous alkaline processing composition as determined, for example, by the hydrophobic/hydrophilic balance or degree of coalescence thereof. In general, increased permeability to alkali or aqueous alkaline processing composition and, thus, a shorter hold time, may be obtained by increasing the hydrophilicity of the matrix polymer or decreasing the degree of coalescence.

In addition to affecting the hold time of the diffusion control layers of this invention, matrix polymers may also be used to modulate the permeability of the layers to alkali or materials soluble or in solubilized by an aqueous alkaline processing composition and thus affect the functionality of the layers within a film unit. For example, relatively hydrophobic matrix polymers or matrix polymers having a relatively high degree of coalescence may help to render diffusion control layers hereof substantially impermeable to alkali until β-elimination occurs, thus providing functionality to such layers as alkali neutralization timing layers or overcoat layers in image-receiving elements and positive components of diffusion transfer film units. Alternatively, relatively hydrophilic matrix polymers or matrix polymers having a relatively low degree of coalescence may help to render diffusion control layers hereof initially permeable to alkali while remaining impermeable to materials soluble in or solubilized by an aqueous alkaline processing composition, e.g., image dye-providing materials, until β-elimination occurs, thus providing functionality to such layers as interlayers or overcoat layers in photosensitive elements and negative components of diffusion transfer film units.

Utilization of matrix polymers can thus provide an alternative or complementary means to the above-mentioned use of suitable comonomers in the β-elimination copolymers hereof as a method of modulating the hold time or functionality of the diffusion control layers of this invention. It will be understood, however, that the β-elimination reaction is necessary to achieve the relatively rapid change in permeability of the layer.

Matrix/β-elimination polymer systems adapted to utilization in a diffusion control layer may be prepared by physical mixing of the respective polymers, or by preparation of the matrix polymer in the presence of the β-elimination polymer. As disclosed in U.S. Pat. No. 4,297,431 of Charles Sullivan, issued Oct. 17, 1981, a preferred matrix/β-elimination polymer system comprises the system whereby a β-elimination polymer is formed in the presence of a preformed matrix polymer. Polymers which may be used as matrix polymers will generally be copolymers which comprise comonomeric units such as acrylic acid; methacrylic acid; methylmethacrylate; 2-acrylamido-2-methylpropane sulfonic acid; acrylamide; methacrylamide; N,N-dimethylacrylamide; ethylacrylate; butylacrylate; diacetone acrylamide; acrylamido acetamide; and methacrylamido acetamide. The comonomeric units, as well as the ratios thereof, should be chosen on the basis of the physical characteristics desired in the matrix polymer and in the diffusion control layer in which it is to be utilized. For example, a more hydrophilic and thus a generally more permeable matrix material can be had by increasing the respective ratio of hydrophilic comonomers, such as acrylic acid or methacrylic acid, within the matrix polymer.

Matrix polymer/β-elimination polymer systems useful in the present invention include those listed below wherein 3-SMA designates 3-sulfolanyl methacrylate MESC designates N-(methacryloxyethyl)-3-sulfolanyl carbamate, DAA designates diacetone acrylamide, BA designates butyl acrylate, AA designates acrylic acid, MA designates methacrylic acid, MMA designates methyl methacrylate and AMPS designates 2-acrylamido-2-methylpropane sulfonic acid. In the matrix systems listed below the specified β-elimination polymer was polymerized in the presence of the specified preformed matrix polymer. All ratios and proportions are in parts by weight:

| Matrix System | Components |
| --- | --- |
| A | 70 parts of a 48.9/42.6/8/0.5 matrix copolymer of DAA/BA/AA/AMPS and 30 parts of 80/20 poly(MESC-co-MMA) |
| B | 70 parts of a 50.5/44/5/0.5 matrix copolymer of DAA/BA/AA/AMPS and 30 parts of 70/30 poly(3-SMA-co-DAA) |
| C | 70 parts of a 48.9/42.6/8/0.5 matrix copolymer of DAA/BA/AA/AMPS and 30 parts of 68.5/29.5/2 poly(3-SMA-co-DAA-co-AA) |
| D | 70 parts of a 48.9/42.6/8/0.5 matrix copolymer of DAA/BA/AA/AMPS and 30 parts of 80/20 poly(3-SMA-co-MA) |

The polymers hereof can be utilized in a number of diffusion transfer products and processes based upon imagewise transfer of a diffusible image-providing material, e.g., a diffusible dye, dye intermediate, or soluble silver complex. The diffusion transfer film units of the present invention comprise as essential layers, a support layer; at least one photosensitive silver halide emulsion layer having associated therewith a diffusion transfer process image-providing material; an alkaline processing composition permeable image-receiving layer; and at least one diffusion control layer comprising the polymers of this invention. Following photoexposure, the silver halide emulsion is developed with an aqueous alkaline processing composition and, as a function of development, an imagewise distribution of diffusible image-providing material is formed which is transferred, at least in part, to the superposed image-receiving layer. The diffusion control layers of such film units may be used to control diffusion of alkali or of the image-providing material in accordance with the disclosures contained herein.

Film units within the present invention include those wherein the silver halide emulsion layers and the image-receiving layer are initially contained in separate elements. Such film units may thus comprise: (a) a photosensitive element comprising a support layer which is preferably opaque and a negative component comprising at least one photosensitive silver halide emulsion layer having associated therewith a diffusion transfer process image-providing material; (b) an image-receiving element comprising a support layer which may be opaque or transparent as appropriate for a given process and a positive component comprising an image-receiving layer; and (c) a diffusion control layer comprising the polymers of this invention in at least one of said photosensitive element or image-receiving element. The respective elements may be brought into superposition subsequent or prior to exposure. Subsequent to exposure, an aqueous alkaline processing composition is distributed between the superposed elements to initiate development. If the image-receiving element provides an opaque reflective background, the image formed may be viewed as a reflection print upon separation of the elements. By using a transparent image-receiving element, the resultant image may be viewed as a transparency upon separation of the elements. Alternatively, if the photosensitive element and/or processing composition contains a light reflecting layer, e.g., a white pigment such as titanium dioxide, the image may be viewed as a reflection print against the background provided by the light-reflecting layer, without separation of the elements. The photosensitive element may also comprise a neutralization layer, e.g., an acid polymer layer, and a timing layer positioned between the support layer and the negative component with the neutralization layer positioned adjacent the support. By conduct of a neutralization reaction between the acid-reactive sites of the neutralization layer and the alkali provided by the processing comosition the environmental pH of the film unit may be lowered, thus providing benefits detailed hereinbelow. The timing layer functions to prevent premature pH reduction by slowing diffusion of the alkali toward the neutralization layer.

The diffusion control layers of this invention can also be used in diffusion transfer film units wherein the photosensitive layers and image-receiving layer are in a single element, i.e. integral negative-positive film units wherein the negative and positive components are contained in a photosensitive laminate or otherwise retained together in a superposed relationship at least prior to exposure. For example, the diffusion control layers herein can be used in integral film units of the type described in detail in U.S. Pat. No. 3,415,644, which film units are particularly adapted for formation of color images. Film units of this type include, for example, those comprising: (a) a photosensitive laminate comprising a composite structure containing, in sequence, an opaque support layer, preferably an actinic radiation-opaque flexible sheet material, a negative component comprising at least one photosensitive silver halide emulsion layer having associated therewith an image dye-providing material, a positive component comprising an image-receiving layer dyeable by the image dye-providing material, and a transparent support layer, preferably an actinic radiation transmissive flexible sheet material, the photosensitive laminate also comprising a diffusion control layer comprising the polymers of the present invention; (b) means retaining an aqueous alkaline processing composition integrated with the film unit so that the processing composition can be distributed betwen the negative and positive components. In this type of film unit a light-reflecting pigment is preferably provided by the processing composition such that the distribution of the processing composition between the negative and positive components provides a light-reflecting layer against which a dye image formed in the image-receiving layer can be viewed without separation of the components.

The diffusion control layers of this invention can also be used in integral negative-positive film units of the type described in U.S. Pat. No. 3,594,165. Film units of this type include, for example, those comprising: (a) a photosensitive laminate comprising, in sequence, a transparent support layer, preferably an actinic radiation transmissive flexible sheet material, a positive component comprising an image-receiving layer, a processing composition permeable, ligh-reflecting layer against which a dye image formed in the image-receiving layer can be viewed, and a negative component comprising at least one photosensitive silver halide emulsion layer having associated therewith an image dye-providing material; (b) a transparent sheet superposed substantially coextensive the surface of the photosensitive laminate opposite the transparent layer; (c) means retaining an aqueous alkaline processing composition, which includes an opacifying agent, integrated with the film unit such that the processing composition can be distributed between the photosensitive laminate and the transparent sheet; and (d) a diffusion control layer comprising a polymer of the present invention, which layer may be a component of the photosensitive laminate or a coating on that side of the transparent sheet contiguous the photosensitive laminate. Color images formed within the image-receiving layer can be viewed against the background of the light-reflecting layer without separation of the transparent sheet from the photosensitive laminate.

Multicolor images may be prepared in the film units of the present invention which comprise at least two selectively sensitized silver halide emulsion layers, each associated with an image dye-providing material which provides an image dye possessing spectral absorption characteristics substantially complementary to the predominant sensitivity range of its associated emulsion. The most commonly employed negative components for forming multicolor images are of the tripack structure and contain blue, green, and red sensitive silver halide layers each having associated therewith in the same or a contiguous layer a yellow, a magenta, and a cyan image dye-providing material respectively. It is preferred that each of the silver halide emulsion layers, and its associated image dye-providing material, be spaced from the remaining emulsion layers, and their associated image dye-providing materials, by separate alkaline solution permeable interlayers, such as those provided by the instant invention.

As disclosed in U.S. Pat. No. 2,983,606 and a number of other patents, image dye-providing materials which are particularly useful in forming color images by diffusion transfer are the dye developers, i.e., compounds which contain, in the same molecule, both the chromophoric system of a dye and also a silver halide developing function. In a typical diffusion transfer system, each dye developer is associated with a separate silver halide emulsion layer and is, most preferably, substantially soluble in the reduced form only at the first pH provided by the processing composition, possessing subsequent to photoexposure or processing a spectral absorption range substantially complementary to the predominant sensitivity range of its associated emulsion. Following photoexposure, the processing composition is applied and permeates the emulsion layers to initiate development of the latent image contained therein. The dye developer is immobilized or precipitated in exposed areas as a consequence of the development of the latent image. In unexposed and partially exposed areas of the emulsion, the dye developer is unreacted and diffusible and thus provides an imagewise distribution of unoxidized dye developer dissolved in the liquid processing composition, as a function of the point-to-point degree of exposure of the silver halide emulsion. At least part of this imagewise distribution of unoxidized dye developer is transferred, by imbibition, to a superposed image-receiving layer, said transfer substantially excluding oxidized dye developer. The image-receiving layer receives a depthwise diffusion, from the developed emulsion, of unoxidized dye developer without appreciably disturbing the imagewise distribution thereof to provide the reversed or positive color image of the developed image. The image-receiving layer may contain agents adapted to mordant or otherwise fix the diffused, unoxidized dye developer. Subsequent to substantial transfer image formation, it is preferred that the environmental pH of the film unit be adjusted downward to a second pH at which the residual dye developers remaining within the negative structure are precipitated or otherwise rendered non-diffusible in either their reduced or oxidized state. The pH adjustment is generally accomplished by means of an acid neutralization layer, preferably a polymeric acid layer, as detailed hereinbelow.

For purposes of illustration, the present invention will hereinafter be described in terms of dye developers which function as described above, although no limitation of the invention to the illustrative image dye-providing materials is intended.

As illustrated in the accompanying drawings, FIG. 1 sets forth a perspective view of an integral film unit of the type described in referenced U.S. Pat. No. 3,415,644, shown with the processing composition 26 distributed between the negative and positive components. Film unit 10 comprises photosensitive laminate 11 including in order, opaque support layer 12; cyan dye developer layer 13; red-sensitive silver halide emulsion layer 14; interlayer 15; magenta dye developer layer 16; green-sensitive silver halide emulsion layer 17; interlayer 18; yellow dye developer layer 19; blue-sensitive silver halide emulsion layer 20; overcoat layer 21; image-receiving layer 22; spacer layer 23; neutralizing layer 24; and transparent support layer 25. Following photoexposure through transparent support layer 25, processing composition 26, initially retained in a rupturable container (not shown) is distributed between overcoat layer 21 and image-receiving layer 22 to initiate development of the silver halide emulsion layers. It is preferred that processing composition 26 contains an opacifying agent of the type described for example, in U.S. Pat. No. 3,647,437, such that the layer of processing composition 26 is able to prevent further exposure of the photosensitive layers of the film unit during the processing of the film unit outside of the camera. As a consequence of development, an imagewise distribution of diffusible dye developer is formed which is transferred, at least, in part to image-receiving layer 22. The layer provided by processing composition 26 preferably comprises a light-reflecting pigment, such as titanium dioxide, against which the color image formed in image-receiving layer 22 can be viewed. Subsequent to substantial transfer image formation, a sufficient portion of the alkali provided by processing composition 26 permeates image-receiving layer 22 and spacer layer 23, to gain access to neutralizing layer 24 whereupon neutralization of the alkali occurs to lower the pH of the system to a level at which the dye developers are insoluble and non-diffusible, to provide thereby a stable color transfer image.

Rather than being positioned between image-receiving layer 22 and support layer 25, spacer layer 23 and neutralizing layer 24 may be disposed intermediate support layer 12 and cyan dye developer layer 13, with neutralizing layer 24 positioned adjacent to support layer 12. In this embodiment, the alkali provided by processing composition 26 permeates layers 13 through 21 and spacer layer 23 to gain access to neutralizing layer 24 whereupon neutralization of the alkali is effected as described hereinabove.

With multicolor diffusion transfer products such as those described above, undesirable inter-image effects may occur whereby a given dye developer or other image dye-providing material is controlled as a result of association with a silver halide emulsion layer other than the one with which it was initially associated in the film unit. This unintended associative relationship generally results from migration of the image dye-providing material to a silver halide layer other than the one with which it is initially associated prior to development of this "wrong" emulsion layer. As a result of this premature migration, the image dye-providing material may acquire diffusion characteristics opposite to those it would normally possess had it remained in association with its intended controlling silver halide layer. For example, if a dye developer prematurely migrates to a silver halide layer other than the one with which it is initially associated, it may undergo oxidation to a non-diffusible species as a function of the development of this "wrong" layer and will be rendered incapable of transferring as intended to the image-receiving layer. As a result, accuracy in color reproduction and color saturation within the transfer image will be adversely affected. In addition, a portion of a second dye developer which should have undergone oxidation as a function of the development of this "wrong layer" remains in a reduced and diffusible state and, thus, may transfer to contaminate the resultant color transfer image. These inter-image effects may be more specifically exemplified by reference to FIG. 1. If it is possible for the magenta dye-developer of layer 16 to back-diffuse to red sensitive silver halide emulsion layer 14 before substantial development of this layer and resultant substantial formation of an imagewise distribution of the cyan dye developer in layer 13, some of the magenta dye developer may become oxidized and rendered non-diffusible as a function of red exposure and development of the red sensitive emulsion layer. Thus, there is produced a loss in magenta dye density in the transfer image. Moreover, that portion of cyan dye developer which should have been oxidized in preference to the magenta dye developer remains in the reduced form and may diffuse to image-receiving layer 22 with resultant cyan dye contamination of the transfer image. Thus, accurate color reproduction of a photographed object is hindered by such inter-image effects.

To obviate or minimize inter-image effects, diffusion control layers hereof may be employed as interlayers positioned between the respective silver halide layers, and their associated dye developers, such as interlayers 15 and 18 in FIG. 1. The β-elimination step undergone by the β-elimination polymer(s) within these layers ensures a delay in permeability of these layers during initial processing of the film unit and thus "holds" the dye developer and substantially prevents diffusion to unassociated silver halide layers at least until after substantial development of these layers and formation of the intended imagewise distributions of the dye developers. The "release" of the diffusible dye developers should occur prior to substantial fogging of the emulsion layer with the most rapid fogging rate. It will be appreciated that the "hold-release" behavior of the interlayers of this invention provides advantages over those interlayers which allow a slow leaking of dye developer at the start of the processing interval in that the dye developers are better confined to their associated emulsion layer during the critical initial development interval and then released rapidly and in substantial quantity so as to allow rapid and essentially simultaneous transfer of the color image-forming materials.

In addition to minimizing the above described inter-image effects, interlayers comprising the polymers of this invention may be used to provide increased capacity for accurate color reproduction over a range of temperatures. In general, the lowering of the temperature at which processing occurs slows both the rate of development and the rate of dye diffusion. If the respective rates are slowed disproportionately, i.e., if the decrease in the development rate is proportionately greater than the decrease in the rate of diffusion, color reproduction may be adversely affected by diffusion of the dye away from its associated emulsion layer prior to substantial development of that layer. This type of premature migration may be minimized by use of interlayers comprising the polymers of this invention which have been found to provide markedly longer "hold" times at lower temperatures, e.g., 7° C. relative to the "hold" time observed at higher temperatures, e.g., 24° C. Thus, the interlayers may be utilized to hold the dye developer in association with the silver halide emulsion for longer time periods at lower temperatures to accommodate the system to slower development rates at these temperatures while allowing for a proportionately faster "release" as the temperature and development rate increase.

The polymers of this invention useful as interlayer materials as described hereinabove can also be utilized in overcoat layers of photosensitive elements or negative component overcoat layers such as overcoat layer 21 in FIG. 1. Such overcoat layers can be used, for example, to prevent premature migration of the dye developer most proximate to the distributed processing composition or to provide a means by which the various color image-forming materials may be made available essentially simultaneously to the mordant sites within the image-receiving layer.

The processing compositions employed in diffusion transfer processes of the type contemplated herein usually are highly alkaline, having a pH in excess of 12 and frequently in excess of 14 or higher. In general, the highly alkaline environment facilitates the conduct of dye diffusion to provide satisfactory diffusion rates and image dye densities. As disclosed in U.S. Pat. No. 3,362,819 it is highly desirable that the environmental pH of the film unit be lowered to at least 11 or lower subsequent to substantial transfer image formation to achieve improved stability of the dye image. U.S. Pat. No. 3,415,644 discloses that in integral film units wherein the negative and positive components remain in a superposed contiguous relationship subsequent to substantial transfer image formation, an in-process adjustment of the environmental pH of the film unit from a pH at which transfer processing is operative to a pH at which dye transfer is inoperative subsequent to substantial transfer image formation is highly desirable in order to achieve a more stable dye transfer image in terms of the chemical and light stability of the image dye molecules and in terms of preventing post-processing transfer of residual image dye-providing materials within the negative structure to the image-receiving layer.

As disclosed in previously referenced U.S. Pat. No. 3,362,819, reduction in the environmental pH of the film unit is preferably achieved by conduct of a neutralization reaction between the alkali provided by the processing composition and a layer comprising immobilized acid reactive sites, i.e., a neutralization layer. Preferred neutralization layers are those comprising a polymeric acid such as cellulose acetate hydrogen phthalate; polyvinyl hydrogen phthalate; polyacrylic acid; polystyrene sulfonic acid; and partial esters of polyethylene/maleic anhydride copolymers.

Premature pH reduction, as evidenced, for example, by a decrease in image dye density, can be prevented by disposing intermediate the neutralization layer and the distributed processing composition a spacer or timing layer which slows diffusion of the alkali toward the neutralization layer. As indicated hereinabove, diffusion control layers of this invention may be used as such timing layers, forming an alkali impermeable barrier for a predetermined time interval and then converting to a relatively alkali permeable condition upon occurrence of $\beta$-elimination to allow the alkali access to the neutralization layer in a rapid and quantitavely substantial fashion.

The timing layers comprising the $\beta$-elimination polymers hereof can be used in image-receiving elements of the type disclosed in U.S. Pat. No. 3,362,819 or as a component part of the positive component of integral negative-positive film units of the type disclosed in previously referenced U.S. Pat. Nos. 3,415,644 and 3,594,165. Alternatively, the timing and neutralization layers may be associated with the negative component as is disclosed, for example, in U.S. Pat. Nos. 3,362,821 and 3,573,043. In film units of the present invention of the type disclosed in referenced U.S. Pat. No. 3,594,165, these layers may also be carried by the transparent sheet employed to facilitate application of the processing composition.

Figure 2:
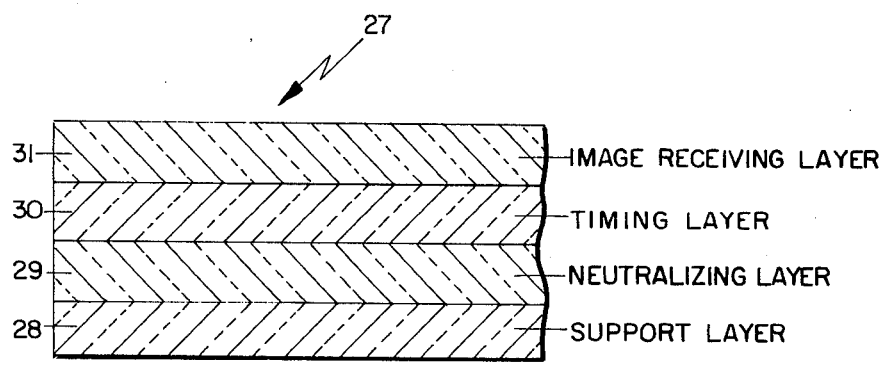
FIG. 2 is a cross-sectional view of an image-receiving element including a diffusion control timing layer of this invention.

Illustrated in FIG. 2 is an image-receiving element of the present invention. Image-receiving element 27 comprises, in order, a support layer 28, a neutralizing layer 29, a spacer or timing layer 30 comprising a $\beta$-elimination polymer of the present invention, and an image-receiving layer 31. During processing the image-receiving layer is situated contiguous the layer of processing composition. The processing composition penetrates image-receiving layer 31 to provide a sufficient pH for image formation therein and is then subsequently neutralized by penetrating through timing layer 30 upon $\beta$-elimination of the diffusion control polymer contained therein to gain access to neutralizing layer 29.

As indicated previously, the permeability of the diffusion control layers of this invention to alkali may be controlled in a predetermined manner by the use of comonomeric units which provide to the polymer a suitable hydrophilic/hydrophobic balance and/or a suitable degree of coalescence or by the use of a matrix material providing the required hydrophilicity or coalescence. In general, increased hydrophobicity and coalescence will render the diffusion control layer relatively less permeable to alkali and to the processing composition prior to the $\beta$-elimination reaction.

In a further embodiment of the present invention, an overcoat layer comprising the polymers hereof may be provided to the image-receiving element or positive component of the film unit contiguous the image-receiving layer and opposite the neutralization layer. Overcoat layers of this type in this position within the film unit may function to control diffusion of alkali or materials soluble in or solubilized by an aqueous alkaline processing composition.

The permeation characteristics of the polymers hereof utilized in timing layers can be evaluated by measuring the time necessary for downward adjustment of the environmental pH to a predetermined lower level as evidenced by color transition of an indicator dye, preferably initially contained in the processing composition, from a colored form at the initially high processing composition pH to a colorless form at said predetermined lower pH level. Evaluations of this type may be carried out utilizing a test structure comprising in order a support, a polymeric acid layer, a test timing layer, and an image-receiving layer. A transparent cover sheet is superposed coextensive the test structure contiguous to the image-receiving layer and an alkaline processing composition comprising an indicator dye which is highly colored at a pH of 12 or higher and colorless below a predetermined lower pH level of about 9 or 10 is spread between the cover sheet and the image-receiving layer. The indicator dye remains colored, and may be viewed as such through the transparent cover sheet, until the alkali penetrates through the test timing layer to gain access to the polymeric acid whereupon neutralization of a substantial portion of the alkali present occurs to lower the pH to a level at which the indicator dye is colorless. The measurement of the time necessary for substantial "clearing" of the indicator is generally referred to as the "clearing time". Test structures comprising timing layers which allow a slow initial leakage of alkali and gradually become more permeable show no precipitous change in color but rather a gradual clearing while structures comprising the timing layers described herein will show a precipitous change in color after an initial delay evidencing the rapid change in alkali permeability undergone by the timing layer upon $\beta$-elimination.

Figure 3:
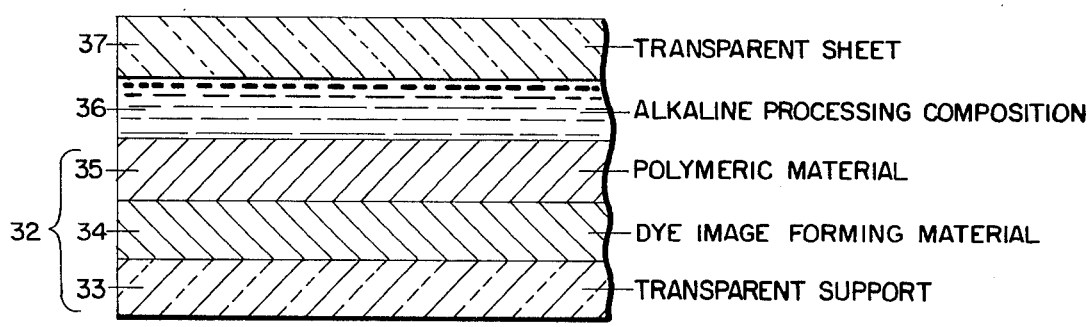
FIG. 3 illustrates a model arrangement for measuring the "hold-time" of interlayers of this invention.

The capacity of diffusion control layers comprising polymers hereof to delay permeation therethrough of dye image-providing materials until conversion by $\beta$-elimination to a relatively dye-permeable condition can be evaluated by utilization of the test structure shown in FIG. 3. In accordance with such structure, transfer of the image dye-providing material through the test diffusion control layer is monitored in relation to time. The "hold-release" properties of the $\beta$-elimination polymer test material can be evaluated in simulation of the functioning of the material, e.g., an interlayer in a photosensitive element. Such test structure and a suitable method of evaluation are set forth in detail in Example 4.

The polymers hereof containing the recurring units of formula (I) can be readily prepared by polymerization in known manner of a corresponding polymerizable monomeric compound of the formula (X):

wherein each of R, L and Z have the meanings as aforedescribed. The polymerizable monomer (X) can be prepared by resort to a variety of synthetic procedures depending, for example, upon the nature of the linking group L. For example, when the linking group L is a carboxylate radical, i.e.,

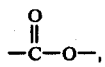

the polymerizable monomer can be suitably prepared by reaction of an unsaturated acid, or anhydride or halide thereof, with an alcohol of the formula Z—OH wherein Z is a cyclic β-elimination moiety as defined previously. Thus, Z can be a β-elimination moiety of the formula (II A) or (II B), such as the moieties of formulas (III A) through (III D) and (IV A) through (IV D), and the cyclic alcohol can be reacted with the unsaturated acid, anhydride or halide.

The production of 3-sulfolanyl methacrylate can be illustrated by the reaction of a mixture of methacrylic acid and trifluoroacetic anhydride with 3-hydroxysulfolane in a trifluoroacetic acid reaction solvent. The compounds 3-sulfolanyl acrylate and 3-sulfolanyl methacrylate and suitable methods for their production are described, for example, in U.S. Pat. No. 3,257,319 (issued June 21, 1966 to R. H. Raines et al.) and by A. H. Ahlbrecht et al., J. Am. Chem. Soc. 75, 984(1952).

Suitable cyclic alcohol compounds Z—OH for production of monomeric compounds of formula (X) where L is the carboxylate linking group include, for example, such alcohols as 3-hydroxy-thietane dioxide; 3-hydroxy-sulfolane, 3-hydroxythiane dioxide; 3-hydroxy-cyclopentanone; 3-hydroxy-cyclohexanone; 1-cyano-2-hydroxy-cyclopentane; 1-hydroxy-2-methylsulfonyl cyclopentane; 1-hydroxy-2-(p-tolyfulfonyl) cyclohexane; and 3-hydroxy-4-(methylsulfonyl)-tetrahydrofuran.

Polymerizable monomers of formula (X) wherein linking group L is a linking group corresponding to formula (V) herein can be prepared, for example, by the reaction of an acrylyl or methacrylyl chloride, anhydride or ester of the formulae

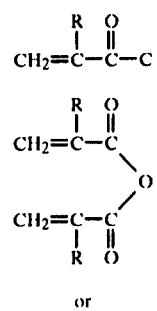

or

-continued

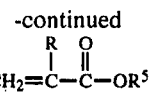

respectively, wherein R is as previously defined and $R^5$ is alkyl or aryl, with a primary or secondary amine of the formula

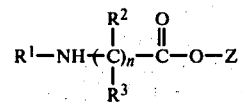

wherein $R^1$, $R^2$, $R^3$, Z and n are as previously defined. The resulting monomeric compound by polymerization provides a polymer comprising recurring units having the formula (VI) hereinbefore.

A preferred method for production of polymerizable monomers of formula (X) where L is linking group of the type represented by formula (V) involves the reaction of a 2-alkenyl-5-oxazalone of the formula

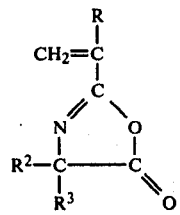

(wherein R, $R^2$ and $R^3$ have the meanings previously provided) with a cyclic alcohol of the formula Z—OH wherein Z is a β-elimination moiety as previously defined, i.e., a β-elimination moiety of formula (II A) or (II B). This reaction is illustrated by the following reaction scheme;

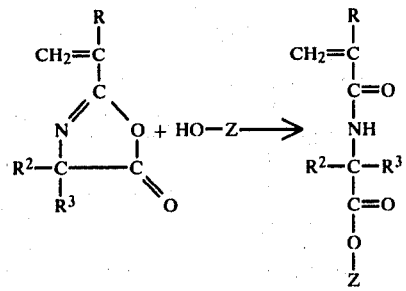

The preparation of polymerizable monomers of formula (X) wherein linking group L corresponds to formula (V) can be suitably effected by employing the synthetic procedures described in U.S. Pat. No. 4,288,523 (issued Sept. 8, 1981 to L. D. Taylor) except that an alcohol of the formula Z—OH as herein defined is utilized in place of the alcohol compounds there utilized. The disclosure of U.S. Pat. No. 4,288,523 is incorporated herein by reference.

Polymerizable compounds of formula (X) wherein linking group L is a carbamate-containing linkage of formula (VII) can be suitably prepared by the reaction of a polymerizable isocyanato ester of acrylic, methacrylic or 2-chloroacrylic acid having the formula (VI):

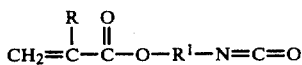

(XI)

(wherein R and R¹ are as previously defined) with an alcohol of the formula Z—OH wherein Z has the aforedescribed meaning. Any of the Z—OH alcohols previously described can be utilized for this purpose. The reaction is illustrated by reference to the following reaction scheme which shows the reaction of β-cyanatoethyl methacrylate and 3-hydroxy sulfolane to form N-(methacryloxyethyl)-3-sulfolanyl carbamate:

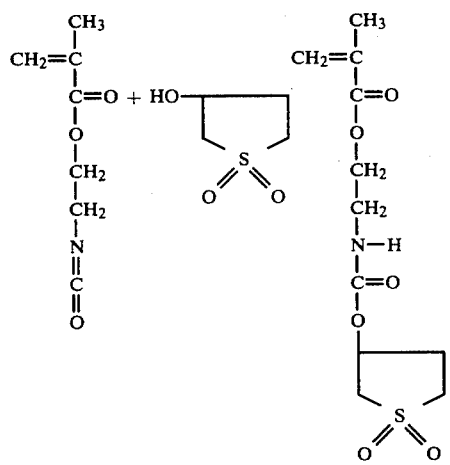

The polymerizable isocyanato esters (XI) utilized as starting materials for the production of the polymerizable monomeric carbamate compounds of the invention include the isocyanatoalkyl esters of such ethylenically unsaturated acids as acrylic acid, methacrylic acid and 2-chloroacrylic acid. Suitable isocyanoalkyl esters are the β-isocyanatoethyl esters such as the β-isocyanatoethyl esters of these ethylenically unsaturated acids. A preferred starting material is β-isocyanatoethyl methacrylate which can be effectively utilized for the production of monomeric carbamate compounds of the invention. The isocyanatoalkyl ester starting materials (IV) are known compounds and their method of preparation is described, for example, in U.S. Pat. No. 2,718,516 (issued Sept. 20, 1955 to N. M. Bortnick).

The monomeric compounds of formula (X) can be prepared in any of a variety of inert solvents. It will be appreciated, for example, that isocyanate groups exhibit reactivity toward compounds having a labile proton and, accordingly, hydroxyl-containing or amine-containing solvent materials will be desirably avoided where compounds having a carbamate-containing linkage are desirably employed. Suitable solvents include tetrahydrofuran, chloroform, dichloromethane, dimethylformamide, benzene, dioxane, toluene, acetone, methylethylketone, and ethyl acetate. The reactions, in general, may be conducted over temperature ranges of about 0° C. to about 100° C. and preferably about 15° C. to about 40° C. but will vary with the particular compound prepared. In general, the reactions can be facilitated by use of a tin catalyst such as stannous octanoate, a tertiary amine catalyst such as triethylamine, a 4-dialkylaminopyridine catalyst, e.g., 4-(N,N-dimethylamino)-pyridine or 4-pyrrolidinopyridine. If desired, a small amount of polymerization inhibitor such as hydroquinone or t-butylpyrocatechol also be present during the reactions.

The monomers prepared by any of the above methods may be polymerized according to different polymerization techniques such as bulk, solution, suspension, or emulsion polymerization. In addition, the polymerization may be conducted in the presence of other suitable polymers, i.e., a polymeric matrix material, to prepare a matrix system which may be used as a diffusion control layer. The polymerization can be initiated chemically, e.g., by suitable free radical or redox initiators or by other means such as heat or incident radiation. As examples of chemical initiators, mention may be made of azobisisobutyronitrile, potassium persulfate, sodium bisulfite, benzoyl peroxide, diacetyl peroxide, hydrogen peroxide, and diazoaminobenzene. It will be appreciated that the chosen means of initiation should be substantially incapable of degrading or otherwise adversely reacting with either the reactants or products of the reaction. The amount of catalyst used and the reaction temperature may be varied to suit particular needs. Generally, the polymerization should proceed satisfactorily by carrying out the reaction at a temperature between 25° C. and 100° C. and using less than 5% by weight of initiator, based on the starting weight of the polymerizable monomer or monomers.

The polymers of the present invention, i.e., the polymers of formula (I) can be prepared by resort to an alternative procedures. Thus, if desired, the monomeric precursor compound can first be polymerized and the resulting polymer can be derivatized by reaction with an alcohol of the formula Z—OH wherein Z has the aforedescribed meaning. This is illustrated by the following reaction scheme:

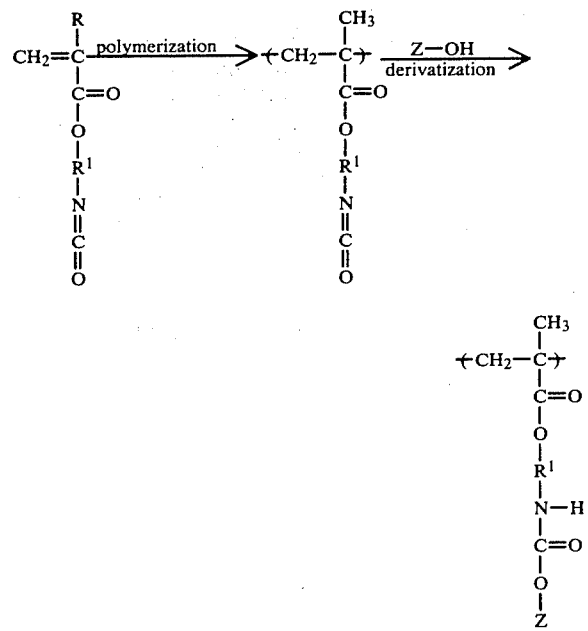

The present invention is further illustrated in the following Examples which are illustrative only and not intended to be of limiting effect. Unless otherwise stated, all parts of percentages are by weight.

EXAMPLE 1

Preparation of N-(methacryloxyethyl)-3-sulfolanyl carbamate

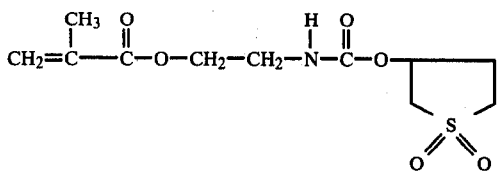

3-hydroxysulfolane (81.70 grams; 0.60 mole) was dissolved in methylene chloride (250 mls.) in a 500-ml., round bottom flash equipped with magnetic stirrer, thermometer and water condenser topped with a drying tube. Anhydrous magnesium sulfate (5.0 grams) and 3-Angstrom, powdered zeolitic molecular sieve material (10.0 grams) were added and the contents were stirred for one hour at room temperature. To the flask was added β-isocyanatoethyl methacrylate (77.58 grams; 0.50 mole) and 6.11 grams (0.05 mole) of 4-(N,N-dimethylamino)pyridine were added in one portion. The resulting exotherm caused boiling of the methylene chloride and an ice bath was utilized to prevent refluxing. The reaction vessel was cooled for about 1.5 hours and was then stirred at room temperature overnight. Total reaction time was about 22.5 hours. The reaction contents were filtered, then stirred with 200 mls. of ice water and four mls. of glacial acetic acid for one-half hour. The aqueous phase was separated and the organic phase was washed sequentially with water (1×200 mls.), brine (1×200 mls.), 1% sodium bicarbonate solution (1×200 mls.), brine (1×200 mls.) and was dried with magnesium sulfate. The product was decolorized with charcoal, filtered and 15 mgs. of 4-methyl-2,6-ditertbutyl phenol were added. A viscous yellow liquid was recovered after evaporation of solvent in vacuo. The product, which slowly crystallized on standing, was dissolved in a minimum of ethyl acetate (about 600 mls. product provided about 800 mls. of solution). Hexane (600 mls.) was added to the cloud point and the solution was cooled to −20° C. An additional 100–150 ml. quantity of hexane was added and the solution was again cooled. A white, solid product was recovered by filtration and was washed with hexane, air and, then, vacuum dried to yield 120.74 grams (82.9% yield) of product having a melting point of 70.5°–71.5° C. Molecular structure was confirmed by nuclear magnetic resonance and thin layer chromatographic techniques.

|  | % C | % H | % N | % S | % O |
|---|---|---|---|---|---|
| Calculated for $C_{11}H_{17}NO_6S$ | 45.35 | 5.88 | 4.81 | 11.01 | 32.95 |
| Found | 45.54 | 6.01 | 4.71 | 10.97 | — |

EXAMPLE 2

Preparation of a matrix system comprising a matrix terpolymer consisting of 48.9 parts by weight of diacetone acrylamide, 42.6 parts by weight of butyl acrylate, 8.0 parts by weight of acrylic acid, and 0.5 parts by weight of 2-acrylamido-2-methylpropane sulfonic acid and a β-elimination copolymer consisting of 68.5 parts by weight of 3-sulfolanyl methacrylate, 29.5 parts by weight of diacetone acrylamide and 2 parts by weight of acrylic acid wherein the ratio by weight of matrix polymer to β-elimination polymer is 70:30.

A mixture of 0.0405 grams of ferrous sulfate heptahydrate, 26.36 grams of a 23.9% by weight dialyzed Dowfax solution (Dowfax 2A1 solution available from the Dow Chemical Company, Midland, Mich.), 16.8 grams of a 100% solution of Triton X-100 (available from Rohm and Haas Corp. Philadelphia, Pa.) and 3.6 liters of water was heated to 65° C. under a nitrogen atmosphere and to this mixture were added simultaneously, in separate streams, over a period of two hours:

(a) a mixture of 1026.8 grams of diacetone acrylamide, 168 grams of acrylic acid, 10.5 grams of 2-acrylamido-2-methylpropane sulfonic acid, 35.15 grams of a 23.9% by weight dialyzed Dowfax solution; and 2.1 liters of water;

(b) 894.7 grams of butylacrylate;

(c) a solution of 7.64 grams of potassium persulfate in 200 milliliters of water; and (d) a solution of 2.89 grams of sodium bisulfite in 100 milliliters of water.

Following completion of the additions, 254.9 grams of the resulting matrix polymer were treated in the following manner. Five grams of water and one gram of dialyzed Dowfax solution were added to the polymeric matrix. The matrix was purged with nitrogen and the temperature was raised to 55° C. Over a period of about 20 minutes, 47.8 grams of 1% sodium hydroxide solution were added in a dropwise manner. The resulting neutralized matrix polymer was held under a nitrogen atmosphere for 30 minutes.

To the neutralized polymeric matrix material prepared as aforedescribed were added simultaneously, in separate streams, over about 45 minutes:

(e) a mixture of 19.11 grams of 3-sulfolanyl methacrylate, 8.22 grams diacetone acrylamide and 0.56 gram of acrylic acid;

(f) a solution of 0.2027 gram of potassium persulfate and 20 milliliters of water; and (g) a solution of 0.1201 gram of sodium bisulfite in 20 milliliters of water.

Following completion of these additions, the temperature of the mixture was maintained at 55° C. for three hours. Yield of 376.9 grams of a matrix system having a solids concentration of 25% by weight.

EXAMPLE 3

Preparation of a matrix system comprising a matrix terpolymer consisting of 48.9 parts by weight of diacetone acrylamide, 42.6 parts by weight of butyl acrylate, 8.0 parts by weight of acrylic acid, and 0.5 parts by weight of 2-acrylamido-2-methylpropane sulfonic acid and β-elimination copolymer consisting of 80 parts by weight of N-(methacryloxyethyl)-3-sulfolanyl carbamate and 20 parts by weight of methyl methacrylate wherein the ratio by weight of matrix polymer to β-elimination polymer is 70:30.

A polymeric matrix was prepared according to the procedure set forth in EXAMPLE 2 except as follows. Upon completion of the addition of streams (a) through (d), 274.5 grams of the resulting matrix polymer were treated in the following manner. Five grams of water and 1.08 grams of 18% dialyzed Dowfax solution were added to the polymer matrix. The matrix was purged with nitrogen and the termperature was raised to 55° C. Over a period of about 20 minutes, 51.5 grams of 1% sodium hydroxide solution were added in a dropwise manner. The resulting neutralized matrix polymer was held under a nitrogen atmosphere fro 30 minutes.

To the neutralized polymeric matrix material prepared as aforedescribed were added simultaneously, in separate streams, over about 45 minutes:

(e) a mixture of 24.18 grams of N-(methacryloxyethyl)-3-sulfolanyl carbamate and 5.82 grams methyl methacrylate;

(f) a solution of 0.2183 gram of potassium persulfate and 20 milliliters of water; and (g) a solution of 0.1293 gram of sodium bisulfite in 20 milliliters of water.

Following completion of these additions, the temperaline was maintained at 55° C. for three hours. Yield of 402 grams of a matrix system having a solids concentration of 25.3% by weight.

EXAMPLE 4

Beta-elimination polymers were evaluated using a test structure, 32 in FIG. 3, comprising a transparent support 33, a layer 34 comprising about 215 mg./m² of a cyan dye developer of the formula

| -continued | |
|---|---|
| Water | 100 g. | was introduced between polymeric test material layer 35 and transparent sheet 37 at a gap of 0.071 mm. Immediately after introduction of the processing composition the optical reflection density to red light of the sample was monitored through transparent support 33 as a function of time by use of a MacBeth Quanta-Log densitometer equipped with a strip-chart recorder. The density measured as a function of time was that of the cyan dye developer in the original dye-containing layer 34 and the cyan dye developer in polymer test layer 35. Dye developer which had diffused through test layer 35 into the processing composition was masked by the titanium dioxide contained therein and, thus, did not contribute to the red absorption. In this manner, the diffusion of dye developer through the test layer and into the processing composition could be monitored.

Figure 4:
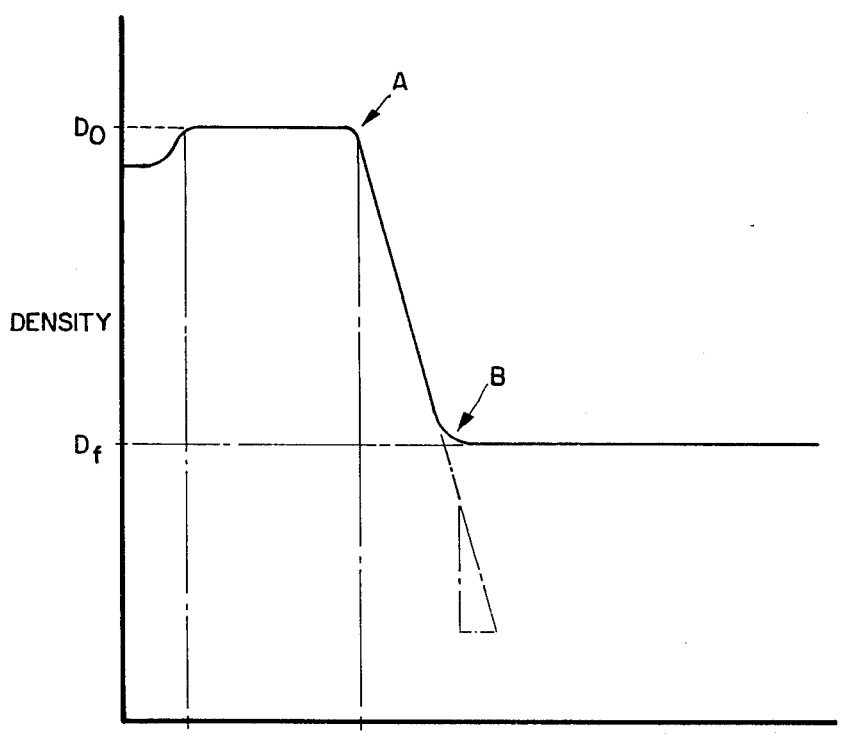
FIG. 4 is a graphical depiction of dye density as a function of time in a system including an interlayer of the present invention.

In FIG. 4 is shown a curve of red absorption density as a function of time where $t_1$ is the time for the cyan

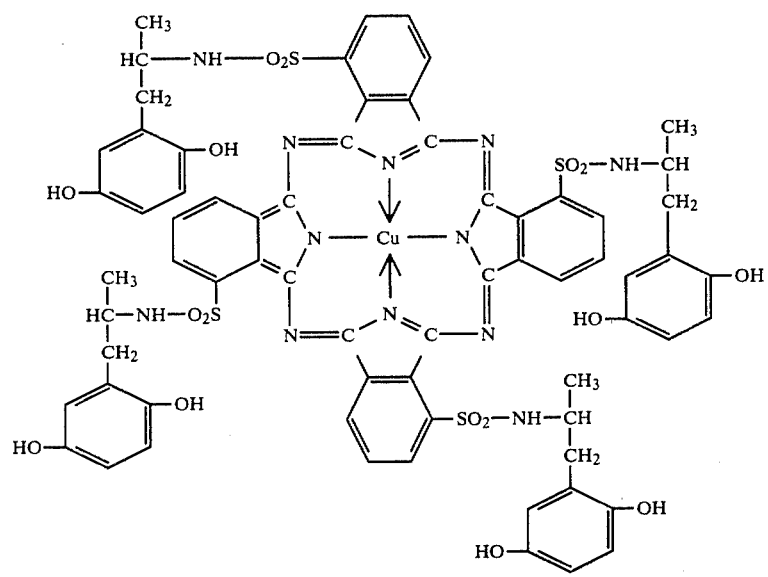

about 430 mg./m² gelatin, and about 16 mg./m² of succindialdehyde and a layer 35 containing about 2150 mg./m² of the polymeric material. Layers 34 and 35 were coated sequentially on support 33 using a conventional loop coater.

A transparent sheet 37 comprising a polyester clear film base was superposed with test structure 32 and an opaque alkaline processing composition 36 comprising:

| Potassium hydroxide (45% aqueous solution) | 23.94 g. |
|---|---|
| Benzotriazole | 1.33 g. |
| 6-Methyl uracil | 0.73 g. |
| Bis-(β-aminoethyl)-sulfide | 0.06 g. |
| Colloidal silica, aqueous dispersion (30% SiO₂) | 4.48 g. |
| Titanium dioxide | 92.12 g. |
| N—phenethyl α-picolinium bromide (50% aqueous solution) | 6.18 g. |
| N—2-hydroxyethyl-N,N'N'—triscarboxymethyl ethylene diamine | 1.82 g. |
| 4-Amino pyrazolo(3,4d)pyrimidine | 0.61 g |
| Carboxymethyl hydroxyethyl cellulose | 4.82 g. | dye developer to become wetted by the processing composition, $t_2$ is the total time the cyan dye developer is held back by the polymer interlayer, $D_o$ is the absorption density after dissolution of the dye developer, and $D_f$ is the final absorption density of the residual dye developer remaining in layers 34 and 35 after completion of dye diffusion. The slope of the line segment between A and B is calculated and serves as an indication of the rapidity with which the test layer undergoes a change in dye permeability.

The polymeric materials prepared as described in EXAMPLES 2 and 3 herein were coated and evaluated as test layer 35 in the above-described test structure. In Table I, the values for $t_1$ and $t_2$ (in seconds) and slope are reported.

TABLE 1

| Polymeric Product | $t_1$ | $t_2$ | Slope |
|---|---|---|---|
| Product of EXAMPLE 2 | 1 | 28 | 330 |
| Product of EXAMPLE 3 | 0.5 | 61 | 135 |

What is claimed is:

1. A photographic diffusion transfer film unit comprising:
   a support layer;
   a photosensitive silver halide emulsion layer having associated therewith a diffusion transfer process image-providing material;
   an alkaline processing composition permeable image-receiving layer; and
   at least one diffusion control layer comprising a polymer having recurring units of the formula

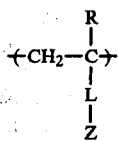

wherein R is hydrogen, halogen or lower alkyl; L is an organic divalent linking group; and Z is a cyclic β-elimination moiety capable under alkaline conditions of undergoing a β-elimination reaction and having the formula

wherein H is a labile proton abstractable under said alkaline conditions, Y is an activating group selected from

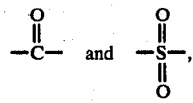

said activating group being effective to activate abstraction of said labile proton under said alkaline conditions and to thereby activate said β-elimination reaction, and A represents the atoms necessary with Y to complete a four- to seven membered ring structure, and D and E are independently hydrogen, methyl or phenyl, provided that not more than one of D and E is methyl or phenyl; or said cyclic β-elimination moiety Z is a moiety having the formula

wherein A and E together represent the atoms necessary to complete with the carbon atoms to which they are bonded a five-, six- or seven-membered ring structure, D is hydrogen, methyl or phenyl, H is a labile proton abstractable under said alkaline conditions and Y is an activating group effective to activate abstraction of said labile proton under said alkaline conditions and to thereby activate said β-elimination reaction.

2. The diffusion transfer film unit of claim 1 wherein said cyclic β-elimination moiety has the formula

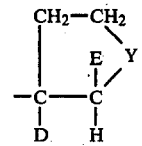

wherein Y is

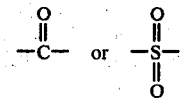

and D and E are each hydrogen, methyl or phenyl, provided that not more than one of D and E is methyl or phenyl.

3. The diffusion transfer film unit of claim 2 wherein Y is

and each of D and E is hydrogen.

4. The diffusion transfer film unit of claim 1 wherein said recurring units have the formula

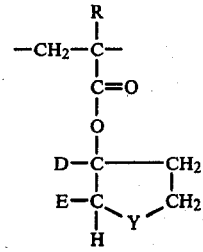

wherein R is hydrogen, halogen or lower alkyl, Y is

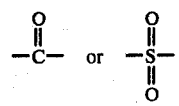

and D and E are each hydrogen, methyl or phenyl, provided that not more than one of D and E is methyl or phenyl.

5. The diffusion transfer film unit of claim 4 wherein R is methyl, Y is

and each of D and E is hydrogen.

6. The diffusion transfer film unit of claim 1 wherein said cyclic β-elimination moiety has the formula

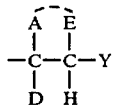

wherein A and E together represent the atoms necessary to complete with the carbon atoms to which they are bonded a five-, six- or seven-membered ring structure, D is hydrogen, methyl or phenyl, and Y is an activating group selected from the group consisting of sulfones of the formula —SO$_2$W wherein W is aryl, aralkyl, alkaryl, alkyl, amino, or substituted amino; carbonyl groups of the formula

wherein T is hydrogen, alkyl, alkoxy, amino, or substituted amino; sulfoxide groups of the formula

wherein G is aryl, alkyl, alkaryl, or aralkyl; nitro and cyano.

7. The diffusion transfer film unit of claim 6 wherein D is hydrogen, A and E together represent —CH$_2$—CH$_2$—CH$_2$— and Y is an activating group of the formula —SO$_2$W where W is alkyl or alkaryl.

8. The diffusion transfer film unit of claim 1 wherein said organic divalent linking group L has the formula

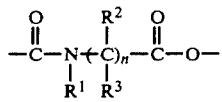

wherein R$^1$ is hydrogen or lower alkyl; R$^2$ and R$^3$ are independently hydrogen, lower alkyl, substituted lower alkyl, aryl, alkaryl, aralkyl, cycloalkyl, or R$^2$ and R$^3$ together with the carbon atoms to which they are bonded constitute a carbocyclic or heterocyclic ring, or R$^3$, when substituted on the methylene carbon atom next adjacent the nitrogen atom, is taken together with R$^1$ to form part of a substituted or unsubstituted N-containing ring; and n is a positive integer of one to six.

9. The diffusion transfer film unit of claim 8 wherein R$^1$ is hydrogen, R$^2$ and R$^3$ are each methyl and n is one.

10. The diffusion transfer film unit of claim 9 wherein said β-elimination moiety Z is a moiety having the formula

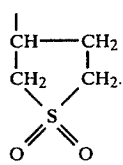

11. The diffusion transfer film unit of claim 1 wherein said diffusion control layer further comprises a matrix polymer.

12. The diffusion transfer film unit of claim 11 wherein said matrix polymer is a copolymer comprising recurring comonomeric units selected from the group consisting of acrylic acid, methacrylic acid; methylmethacrylate; 2-acrylamido-2-methylpropane sulfonic acid; acrylamide; methacrylamide; N,N-dimethylacrylamide; ethylacrylate; butylacrylate; diacetone acrylamide; acrylamido acetamide; and methacrylamido acetamide.

13. The diffusion transfer film unit of claim 1 wherein said image-providing material is a dye developer.

14. The diffusion transfer film unit of claim 1 comprising at least two selectively sensitized silver halide emulsion layers, each associated with an image dye-providing material which provides an image dye possessing spectral absorption characteristics substantially complementary to the predominant sensitivity range of its associated emulsion, wherein said diffusion control layer is an interlayer positioned between said silver halide emulsion layers, and their associated image dye-providing materials.

15. The diffusion transfer film unit of claim 1 wherein said diffusion control layer comprises an alkali neutralization timing layer.

16. The diffusion transfer film unit of claim 1 wherein said diffusion control layer comprises a negative component overcoat layer.

17. The diffusion transfer film unit of claim 1 wherein said diffusion control layer comprises a positive component overcoat layer.

18. A photosensitive element for use in diffusion transfer photographic processes comprising:
a support layer;
a negative component comprising at least one photosensitive silver halide emulsion layer having associated therewith a diffusion transfer process image-providing material; and
at least one diffusion control layer comprising a polymer having recurring units of the formula

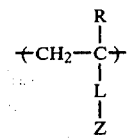

wherein R is hydrogen, halogen or lower alkyl; L is an organic divalent linking group; and Z is a cyclic β-elimination moiety capable under alkaline conditions of undergoing a β-elimination reaction and having the formula

wherein H is a labile proton abstractable under said alkaline conditions, Y is an activating group selected from

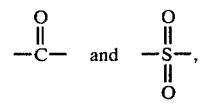

said activating group being effective to activate abstraction of said labile proton under said alkaline conditions and to thereby activate said β-elimination reaction, and A represents the atoms necessary with Y to complete a four- to seven membered ring structure, and D and E are independently hydrogen, methyl or phenyl, provided that not more than one of D and E is methyl or phenyl; or said cyclic β-elimination moiety Z is a moiety having the formula

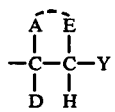

wherein A and E together represent the atoms necessary to complete with the carbon atoms to which they are bonded a five-, six- or seven-membered ring structure, D is hydrogen, methyl or phenyl, H is a labile proton abstractable under said alkaline conditions and Y is an activating group effective to activate abstraction of said labile proton under said alkaline conditions and to thereby activate said β-elimination reaction.

19. The photosensitive element of claim 18 wherein said cyclic β-elimination moiety has the formula

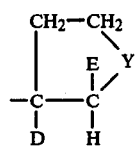

wherein Y is

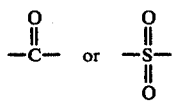

and D and E are each hydrogen, methyl or phenyl, provided that not more than one of D and E is methyl or phenyl.

20. The photosensitive element of claim 19 wherein Y is

and each of D and E is hydrogen.

21. The photosensitive element of claim 18 wherein said recurring units have the formula

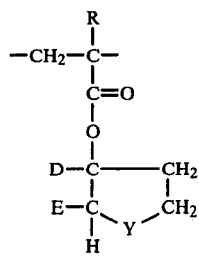

wherein R is hydrogen, halogen or lower alkyl, Y is

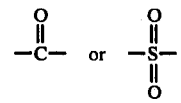

and D and E are each hydrogen, methyl or phenyl, provided that not more than one of D and E is methyl or phenyl.

22. The photosensitive element of claim 21 wherein R is methyl, Y is

and each of D and E is hydrogen.

23. The photosensitive element of claim 18 wherein said cyclic β-elimination moiety has the formula

wherein A and E together represent the atoms necessary to complete with the carbon atoms to which they are bonded a five-, six- or seven-membered ring structure, D is hydrogen, methyl or phenyl, and Y is an activating group selected from the group consisting of sulfones of the formula $-SO_2W$ wherein W is aryl, aralkyl, alkaryl, alkyl, amino, or substituted amino; carbonyl groups of the formula

wherein T is hydrogen, alkyl, alkoxy, amino, or substituted amino; sulfoxide groups of the formula

wherein G is aryl, alkyl, alkaryl, or aralkyl; nitro and cyano.

24. The photosensitive element of claim 23 wherein D is hydrogen, A and E together represent $-CH_2-CH_2-CH_2-$ and Y is an activating group of the formula $-SO_2W$ where W is alkyl or alkaryl.

25. The photosensitive element of claim 18 wherein said organic divalent linking group L has the formula

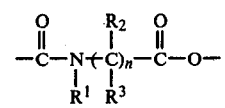

wherein $R^1$ is hydrogen or lower alkyl; $R^2$ and $R^3$ are independently hydrogen, lower alkyl, substituted lower alkyl, aryl, alkaryl, aralkyl, cycloalkyl, or $R^2$ and $R^3$ together with the carbon atoms to which they are bonded constitute a carbocyclic or heterocyclic ring, or $R^3$, when substituted on the methylene carbon atom next adjacent the nitrogen atom, is taken together with $R^1$ to form part of a substituted or unsubstituted N-containing ring; and n is a positive integer one to six.

26. The photosensitive element of claim 25 wherein $R^1$ is hydrogen, $R^2$ and $R^3$ are each methyl and n is one.

27. The photosensitive element of claim 26 wherein said β-elimination moiety Z is a moiety having the formula

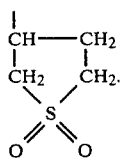

28. The photosensitive element of claim 18 wherein said diffusion control layer further comprises a matrix polymer.

29. The photosensitive element of claim 28 wherein said matrix polymer is a copolymer comprising recurring comonomeric units selected from the group consisting of acrylic acid; methacrylic acid; methylmethacrylate; 2-acrylamido-2-methylpropane sulfonic acid; acrylamide; methacrylamide; N,N-dimethylacrylamide; ethylacrylate; butylacrylate; diacetone acrylamide; acrylamido acetamide; and methacrylamido acetamide.

30. The photosensitive element of claim 18 wherein said image-providing material is a dye developer.

31. The photosensitive element of claim 18 comprising at least two selectively sensitized silver halide emulsion layers, each associated with an image dye-providing material which provides an image dye possessing spectral absorption characteristics substantially complementary to the predominant sensitivity range of its associated emulsion, wherein said diffusion control layer is an interlayer positioned between said silver halide emulsion layers, and their associated image dye-providing materials.

32. The photosensitive element of claim 31 further comprising a neutralization layer and a timing layer positioned between said support layer and said negative component, with the neutralization layer positioned adjacent said support layer.

33. The photosensitive element of claim 18 wherein said diffusion control layer comprises an overcoat layer.

34. An image-receiving element comprising:
a support layer;
a neutralizing layer;
a diffusion control layer comprising a polymer having recurring units of the formula

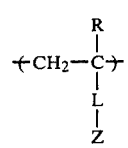

wherein R is hydrogen, halogen or lower alkyl; L is an organic divalent linking group; and Z is a cyclic β-elimination moiety capable under alkaline conditions of undergoing a β-elimination reaction and having the formula

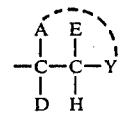

wherein H is a labile proton abstractable under said alkaline conditions, Y is an activating group selected from

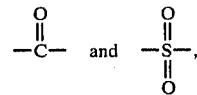

said activating group being effective to activate abstraction of said labile proton under said alkaline conditions and to thereby activate said β-elimination reaction, and A represents the atoms necessary with Y to complete a four- to seven membered ring structure, and D and E are independently hydrogen, methyl or phenyl, provided that not more than one of D and E is methyl or phenyl; or said cyclic β-elimination moiety Z is a moiety having the formula

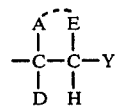

wherein A and E together represent the atoms necessary to complete with the carbon atoms to which they are bonded a five-, six- or seven-membered ring structure, D is hydrogen, methyl or phenyl, H is a labile proton abstractable under said alkaline conditions and Y is an activating group effective to activate abstraction of said labile proton under said alkaline conditions and to thereby activate said β-elimination reaction; and
an image-receiving layer.

35. The image-receiving element of claim 34 wherein said cyclic β-elimination moiety has the formula

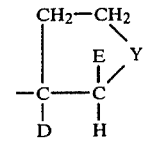

wherein Y is

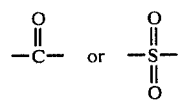

and D and E are each hydrogen, methyl or phenyl, provided that not more than one of D and E is methyl or phenyl.

36. The image-receiving element of claim 34 wherein said recurring units have the formula

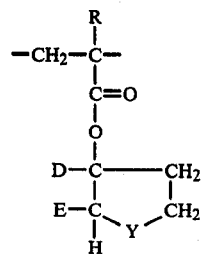

wherein R is hydrogen, halogen or lower alkyl, Y is

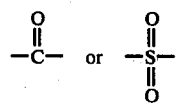

and D and E are each hydrogen, methyl or phenyl, provided that not more than one of D and E is methyl or phenyl.

37. The image-receiving element of claim 36 wherein R is methyl, Y is

and each of D and E is hydrogen.

38. The image-receiving element of claim 34 wherein D is hydrogen, A and E together represent —CH$_2$—CH$_2$—CH$_2$— and Y is an activating group of the formula —SO$_2$W where W is alkyl or alkaryl.

39. The image-receiving element of claim 34 wherein said diffusion control layer comprises an alkali neutralization timing layer.

40. The image-receiving element of claim 34 wherein said diffusion control layer comprises an overcoat layer.

41. An integral negative-positive diffusion transfer film unit comprising:

a photosensitive laminate comprising a composite structure containing, in sequence, an opaque support layer, a negative component comprising at least one photosensitive silver halide emulsion layer having associated therewith an image dye-providing material, a positive component comprising an image-receiving layer dyeable by the image dye-providing material, and a transparent support layer, the photosensitive laminate also comprising a diffusion control layer containing a polymer comprising recurring units of the formula

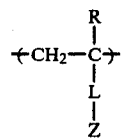

wherein R is hydrogen, halogen or lower alkyl; L is an organic divalent linking group; and Z is a cyclic β-elimination moiety capable under alkaline conditions of undergoing a β-elimination reaction and having the formula

wherein H is a labile proton abstractable under said alkaline conditions, Y is an activating group selected from

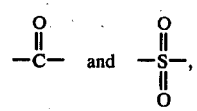

said activating group being effective to activate abstraction of said labile proton under said alkaline conditions and to thereby activate said β-elimination reaction, and A represents the atoms necessary with Y to complete a four- to seven-membered ring structure, and D and E are independently hydrogen, methyl or phenyl, provided that not more than one of D and E is methyl or phenyl; or said cyclic β-elimination moiety Z is a moiety having the formula

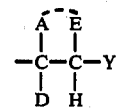

wherein A and E together represent the atoms necessary to complete with the carbon atoms to which they are bonded a five-, six- or seven-membered ring structure, D is hydrogen, methyl or phenyl, H is a labile proton abstractable under said alkaline conditions and Y is an activating group effective to activate abstraction of said labile proton under said alkaline conditions and to thereby activate said β-elimination reaction; and means retaining an aqueous alkaline processing composition integrated with the film unit so that the processing composition can be distributed between the negative and positive components.

42. The diffusion transfer film unit of claim 41 wherein said processing composition comprises a light reflecting pigment such that distribution of the processing composition between the negative and positive components provides a light reflecting layer against which a dye image formed in said image-receiving layer can be viewed.

43. The diffusion transfer film unit of claim 41 further comprising a neutralization layer and a timing layer positioned between said opaque support layer and said negative component, with the neutralization layer positioned adjacent said opaque support layer.

44. The diffusion transfer film unit of claim 41 wherein said cyclic β-elimination moiety has the formula

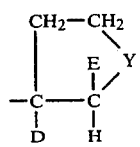

wherein Y is

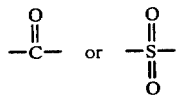

and D and E are each hydrogen, methyl or phenyl, provided that not more than one of D and E is methyl or phenyl.

45. The diffusion transfer film unit of claim 44 wherein Y is

and each of D and E is hydrogen.

46. The diffusion transfer film unit of claim 41 wherein said recurring units have the formula

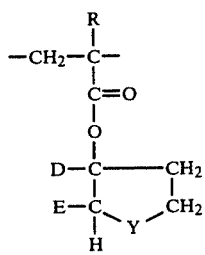

wherein R is hydrogen, halogen or lower alkyl, Y is

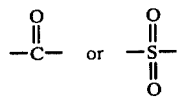

and D and E are each hydrogen, methyl or phenyl, provided that not more than one of D and E is methyl or phenyl.

47. The diffusion transfer film unit of claim 46 wherein R is methyl, Y is

and each of D and E is hydrogen.

48. The diffusion transfer film unit of claim 41 wherein said organic divalent linking group L has the formula

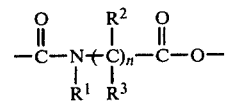

wherein $R^1$ is hydrogen or lower alkyl; $R^2$ and $R^3$ are independently hydrogen, lower alkyl, substituted lower alkyl, aryl, alkaryl, aralkyl, cycloalkyl, or $R^2$ and $R^3$ together with the carbon atom to which they are bonded constitute a carbocyclic or heterocyclic ring, or $R^3$, when substituted on the methylene carbon atom next adjacent the nitrogen atom, is taken together with $R^1$ to form part of a substituted or unsubstituted N-containing ring; and n is a positive integer of one to six.

49. The diffusion transfer film unit of claim 48 wherein $R^1$ is hydrogen, $R^2$ and $R^3$ are each methyl and n is one.

50. The diffusion transfer film unit of claim 49 wherein said β-elimination moiety Z is a moiety having the formula

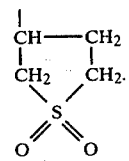

51. An integral negative-positive film unit comprising:

a photosensitive laminate comprising, in sequence, a transparent support layer, a positive component comprising an image-receiving layer, a processing composition permeable, light-reflecting layer against which a dye image formed in said image-receiving layer can be viewed, and a negative component comprising at least one photosensitive silver halide emulsion layer having associated therewith an image dye-providing material;

a transparent sheet superposed substantially coextensive with the photosensitive laminate opposite the transparent layer;

means retaining an aqueous alkaline processing composition, which includes an opacifying agent, integrated with the film unit such that the processing composition can be distributed between the photosensitive laminate and the transparent sheet; and a diffusion control layer comprising a polymer comprising recurring units of the formula

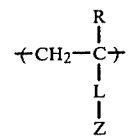

wherein R is hydrogen, halogen or lower alkyl; L is an organic divalent linking group; and Z is a cyclic β-elimination moiety capable under alkaline conditions of undergoing a β-elimination reaction and having the formula

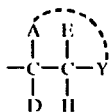

wherein H is a labile proton abstractable under said alkaline conditions, Y is an activating group selected from

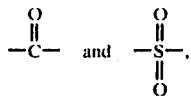

said activating group being effective to activate abstraction of said labile proton under said alkaline conditions and to thereby activate said β-elimination reaction, and A represents the atoms necessary with Y to complete a four- to seven-membered ring structure, and D and E are independently hydrogen, methyl or phenyl, provided that not more than one of D and E is methyl or phenyl; of said cyclic β-elimination moiety Z is a moiety having the formula

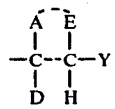

wherein A and E together represent the atoms necessary to complete with the carbon atoms to which they are bonded a five-, six- or seven-membered ring structure, D is hydrogen, methyl or phenyl, H is a labile proton abstractable under said alkaline conditions and Y is an activating group effective to activate abstraction of said labile proton under said alkaline conditions and to thereby activate said β-elimination reaction;

said diffusion control layer being contained within said film unit as either a component of said photosensitive laminate or a coating on that side of said transparent sheet contiguous the photosensitive laminate.

52. The diffusion transfer film unit of claim 51 wherein said recurring units have the formula

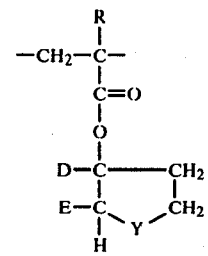

wherein R is hydrogen, halogen or lower alkyl, Y is

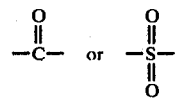

and D and E are each hydrogen methyl or phenyl, provided that not more than one of D and E is methyl or phenyl.

* * * * *